United States Patent
Marshall et al.

(10) Patent No.: US 9,321,837 B2
(45) Date of Patent: Apr. 26, 2016

(54) METHOD FOR THE TREATMENT OF GLOMERULONEPHRITIS BY ADMINISTERING AN IL-6 ANTIBODY

(75) Inventors: Diane Marshall, Slough (GB); Stevan Shaw, Slough (GB)

(73) Assignee: UCB PHARMA S.A., Brussels (BE)

( * ) Notice: Subject to any disclaimer, the term of this patent is extended or adjusted under 35 U.S.C. 154(b) by 287 days.

(21) Appl. No.: 12/676,297

(22) PCT Filed: Sep. 4, 2008

(86) PCT No.: PCT/GB2008/003046
§ 371 (c)(1),
(2), (4) Date: Jun. 29, 2010

(87) PCT Pub. No.: WO2009/030936
PCT Pub. Date: Mar. 12, 2009

(65) Prior Publication Data
US 2010/0310564 A1    Dec. 9, 2010

(30) Foreign Application Priority Data
Sep. 6, 2007  (GB) .................................. 0717337.0

(51) Int. Cl.
*A61K 39/395* (2006.01)
*C07K 16/24* (2006.01)
*C07K 16/28* (2006.01)
*A61K 39/00* (2006.01)

(52) U.S. Cl.
CPC ........... *C07K 16/248* (2013.01); *C07K 16/2866* (2013.01); *A61K 2039/505* (2013.01)

(58) Field of Classification Search
CPC ............ A61K 38/00; A61K 2039/505; A61K 39/0011
USPC .......................................... 424/139.1, 193.1
See application file for complete search history.

(56) References Cited

U.S. PATENT DOCUMENTS 5,116,964 A * 5/1992 Capon et al. ................. 536/23.5
5,670,373 A * 9/1997 Kishimoto ................... 435/334

OTHER PUBLICATIONS

Liang et al., "Anti-interleukin-6 monoclonal antibody inhibits autoimmune responses in a murine model of systemic lupus erythematosus.", Immunology, 2006, 119(3), 296-305.
Cross et al., "The roles of interleukin-6 and interleukin-10 in B cell hyperactivity in systemic lupus erythematosus.", Inflammation Research: Official Journal of the European Histamine Research Society, 1999, 48(5), 255-261.
Horii et al., "Involvement of IL-6 in mesangial proliferative glomerulonephritis.", Journal of Immunology, 1989, 143 (12), 3949-3955.
Kubo et al., "Adrenomedullin gene transcription is decreased in peripheral blood mononuclear cells of patients with IgA nephropathy.", Nephron, 2000, 85(3), 201-206.
http://en.wikipedia.org/wiki/Glomerulonephritis, downloaded Dec. 27, 2011.
http://en.wikipedia.org/wiki/Rapidly_progressive_ glomerulonephritis, downloaded Dec. 27, 2011.
Seo et al, "The Antineutrophil Cytoplasmic Antibody—Associated Vasculitides", Am. J, Med., 117:39-50 (2004).
Weening et al, "The Classification of Glomerulonephritis in Systemic Lupus Erythematosus Revisited", J. Am. Soc. Nephrol, 15: 241-50 (2004).
Merkle et al , "Chronic urticaria and mesangial proliferative glomerulonephritis a case report", Nephrol. Dial Transplant, 22: 3327-3329 (2007).
Levy et al., "Clinical features and outcome of patients with both ANCA and anti-GBN antibodies.", Kidney International 66: 1535-1540, 2004.
Kitching, et al., "Targeting Leukocytes in Immune Glomerular Disease", Current Medicinal Chemistry, 25:448-458 (2008).
Couser, American Journal of Kidney Diseases, vol. XI, No. 6 (Jun.), 1988; p. 450, Table 1.

* cited by examiner

*Primary Examiner* — Prema Mertz
(74) *Attorney, Agent, or Firm* — McDonnell Boehnen Hulbert & Berghoff LLP

(57) ABSTRACT

The present invention provides a method for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement comprising administering a therapeutically effective amount of agent which interacts with or modulates the expression or activity of a mammalian IL-6 polypeptide.

9 Claims, 3 Drawing Sheets

METHOD FOR THE TREATMENT OF GLOMERULONEPHRITIS BY ADMINISTERING AN IL-6 ANTIBODY

This application is a U.S. national phase of International Application No. PCT/GB2008/003046 filed on Sep. 4, 2008, the disclosure of which is incorporated herein by reference in its entirety.

The present invention relates to a new therapeutic use for agents which interact with or modulate the expression or activity of IL-6. More particularly, the invention concerns the use of such agents in the therapy of certain glomerulonephritic disorders. Specifically, the invention provides methods for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement, said treatment and/or prophylaxis comprising targeting and regulation of the polypeptide IL-6, and agents which interact with or modulate the expression or activity of the polypeptide and/or which modulate the maturation of B-cells into antibody producing cells (Hirano et al., 1986 Nature 324, 73-76).

IL-6 has been shown to play a central role in immune regulation, inflammation, haematopoiesis and oncogenesis. Within the immune system, IL-6 induces B-cell antibody production increasing the amount of polyclonal immunoglobulin. It also induces interleukin-2 (IL-2) receptor expression on T-cells (Nomo et al., 1987, Immunol. letters, 15, 3, 249-253) and promotes IL-2 production in activated T-cells thereby inducing both the growth and the differentiation of cytototoxic T-cells (Okada et al., 1988 J. Immunol, 141, 5, 1543-1549). IL-6 is also known to determine the differentiation of monocytes into macrophages (Chomarat et al., 2000 Nature Immunol., 6:510-514).

The function of IL-6 is not restricted to the immune response as it acts in hematopoiesis, thrombopoiesis, osteoclast formation, elicitation of hepatic acute phase response resulting in the elevation of C-reactive protein (CRP) and serum amyloid A (SAA) protein. It is known to be a growth factor for epidermal keratinocytes, renal mesangial cells, myeloma and plasmacytoma cells (Grossman et al., 1989 Proc. Natl. Acad. Sci., 86, (16) 6367-6371; Horii et al., 1989, J. Immunol, 143, 12, 3949-3955; Kawano et al., 1988, Nature 332, 6159, 83-85). IL-6 is produced by a wide range of cell types including monocytes/macrophages, fibroblasts, epidermal keratinocytes, vascular endothelial cells, renal mesangial cells, glial cells, chondrocytes, T and B-cells and some tumour cells (Akira et al., 1990, FASEB J., 4, 11, 2860-2867). Except for tumour cells that constitutively produce IL-6, normal cells do not express IL-6 unless appropriately stimulated.

The IL-6 receptor, IL-6R, binds IL-6 with low affinity. Because IL-6R does not have an intracellular signal transduction domain, ligation alone of IL-6 to IL-6R does not lead to cellular activation as the signal transducing element, gp130, is also required. Similarly, cell surface expression of IL-6R does not mean the cell is responsive to IL-6 stimulation. Proteolytic cleavage leads to the release of soluble IL-6R (sIL-6R; sgp80) which can bind circulating IL-6 and increase the half-life of IL-6. Both cell-bound and soluble IL-6R contribute to cellular activation. IL-6 signaling through cell bound IL-6R has been termed cis signaling whilst cellular activation via soluble IL-6R has been described as trans signaling. Cells expressing gp130 but not IL-6R can be stimulated by IL-6 through sIL-6R.

Neutralising and blocking antibodies to IL-6 are known (Kalai et al., 1997, Eur. J. Biochem. 249, 690-700; Brakenhoff et al., 1990, Journal of Immunology, 145, 561-568; Wendling et al., 1993, J. Rheumatology, 29, 259-262; U.S. Pat. No. 5,856,135) as are neutralising auto-antibodies (Hansen et al, Eur. J. Immunol, 1995, 25, 348-354). Therapeutic antibodies to IL-6R have also been described (WO2004039826 & Kishimoto, 2005, Ann. Rev. Immunol. 23:1-21), the latter reference describing efficacy in rheumatoid arthritis. It has also been reported that the same antibody has shown efficacy in a phase II study of Crohn's disease. Efficacy has also been demonstrated with both anti-IL-6 and anti-IL-6R antibodies in lupus-like disease in NZB/W F1 mice (Fink et al., 1994 J. Clin. Invest. 94, 585; Mihara et al., 1998, Clin. Exp. Immunol. 112, 397) and neutralizing antibody to the murine IL-6 receptor suppressed colitis in an adoptive transfer model of disease (Yamamoto et al., 2000, J. Immunol. 164, 4878; Atreya et al., 2000 Nature Med. 6, 583).

Goodpasture's syndrome is an autoimmune disease which is characterised by deposition of antibodies to the glomerular basement membrane (gbm) along with complement, a progressive glomerulonephritis and often renal failure. Cross reaction with the basement membrane in the lungs causes pulmonary haemorrhage. Goodpasture's syndrome affects mostly young, white men with a male preponderance of between 2 and 9 to 1. It affects both sexes equally in children. Classification can be difficult in that sometime either the lungs or the kidneys are affected but not both. However, the presence of autoantibodies to the glomerular basement membrane is the diagnostic feature with the characteristic pathologic feature being a crescentic glomerulonephritis, with the majority of glomeruli showing crescents of a similar age (Salama & Pusey, 2002, Curr. Opin. Nephrology and Hypertension, 11:279-286).

In general, three types of treatment for Goodpasture's syndrome are used. Non-drug treatment includes intubation, assisted ventilation and haemodialysis, which are often required in the acute phase. Repeated plasmapheresis removes anti-glomerular basement membrane antibodies from the circulation. However, most cases progress to end stage renal failure within months. End-stage renal disease can be managed by long-term haemodialysis. Drug treatment includes high-dose corticosteroids with cyclophosphamide or azathioprine. The duration of immunosuppressive therapy varies considerably and may be necessary for longer than 12 to 18 months in some patients. In respect of surgical treatments, cessation of pulmonary haemorrhage has been described after bilateral nephrectomy. Renal transplantation has also been used to manage end-stage disease. Because of the severe nature of these remedies, more specific and directed therapies are needed for the treatment of glomerulonephritis associated with Goodpasture's syndrome.

Vasculitis includes systemic and small vessel vasculitis such as that associated with diseases with anti-neutrophil circulating antibodies, for example, Wegener's disease (also called Wegener's granulomatosus). Wegener's disease involves inflammation of the arteries of the lungs, nasal passages and kidneys.

IgA nephropathy (IgAN, also known as Berger's disease) is a kidney disease, which affects the glomerulus. IgA nephropathy is the commonest glomerulonephritis with IgA deposits found in the glomerulus. Although much research is ongoing, it is still not understood why IgA is deposited in the kidneys and why it can cause problems such as chronic renal failure.

Whether IL-6 plays any role in the pathogenesis of Goodpasture's syndrome, Wegener's disease or IgA nephropathy was not known hitherto.

The present invention is based on the surprising finding that IL-6 represents a therapeutic target for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement. The invention demonstrates that inhibitors of IL-6 activity are active in an animal model of Goodpasture's syndrome. Specifically, it has been demonstrated that an anti-IL-6 antibody that inhibits IL-6 activity is active in animal models of Goodpasture's syndrome.

Accordingly, the invention provides a method for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement comprising administering a therapeutically effective amount of an agent which interacts with or modulates the expression or activity of IL-6. Also provided is the use of an agent which interacts with or modulates the expression or activity of IL-6 for the manufacture of a medicament for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement.

In the present application, the term "Goodpasture's syndrome" includes lung purpura with nephritis syndrome, anti-gbm nephritis, and anti-gbm nephritis with pulmonary haemorrhage. Accordingly, the methods of treatment described herein also include a method for the treatment and/or prophylaxis of glomerulonephritis associated with lung purpura, anti-gbm nephritis, and/or anti-gbm nephritis with pulmonary haemorrhage.

Agents which interact with or modulate the expression or activity of the activity of IL-6 are referred to hereafter as "inhibitors" of IL-6 activity, in particular the activity or expression of IL-6 in one or more disorders selected from the group consisting of Goodpasture's syndrome, a vasculitic disorder, Wegener's disease, IgA nephropathy and an inflammatory disease with basement membrane involvement. Particularly preferred are agents which interfere with the activity of IL-6 in Goodpasture's syndrome, most preferably Goodpasture's syndrome in humans. Inhibitors (agents) according to the present invention may partially or completely inhibit IL-6 activity. Inhibitors of use in the present invention include without limitation, inhibitors that are capable of interacting with (e.g. binding to, or recognising) IL-6 or the IL-6R or a nucleic acid molecule encoding IL-6 or IL-6R, or are capable of inhibiting the expression of IL-6 or IL-6R or are capable of inhibiting the interaction between IL-6 and IL-6R or are capable of inhibiting the interaction of IL-6 and gp130 or are capable of inhibiting the interaction between IL-6/IL-6R complex and gp130.

Inhibitors of IL-6 activity are well known in the art, as are methods of identifying and producing such inhibitors. Such inhibitors may be, without limitation, antibodies, nucleic acids (e.g. DNA, RNA, antisense RNA and siRNA), carbohydrates, lipids, proteins, polypeptides, peptides, peptidomimetics, small molecules and other drugs. Examples of suitable inhibitors include, but are not limited to, a synthetic functional fragment of the IL-6R that binds to IL-6 and interferes with binding to the native IL-6, an antibody that binds to IL-6 or to the IL-6R and interferes with IL-6R-ligand interaction, an antibody that binds to IL-6 and interferes with the IL-6-gp130 interaction, an antisense nucleic acid molecule that specifically hybridizes to mRNA encoding IL-6 or IL-6R or a small molecule, e.g. NCE, or other drug which inhibits the activity of IL-6, or IL-6R. Thus, agents of use in the methods of the invention include, without limitation, agents that are capable of interacting with (e.g. binding to, or recognising) IL-6 or a nucleic acid molecule encoding an IL-6 polypeptide, or are capable of modulating the interaction, expression, or activity of IL-6 or the expression of a nucleic acid molecule encoding an IL-6 polypeptide.

Inhibitors of IL-6 activity are well known in the art, as are methods of identifying and producing such inhibitors. Examples include, avimers, see for example, Silverman et al., 2005, Nat. Biotechnol. 23(12):1556-61; antibodies such as tocilizumab (Chugai Pharmaceutical Co. Ltd.); CNTO-328 (Centocor Inc.); and sgp130/sIL-6R alpha fusion proteins (Conaris Research Institute AG). Thus, examples of candidate agents include, but are not limited to, antibodies, nucleic acids (e.g. DNA and RNA), carbohydrates, lipids, proteins, polypeptides, peptides, peptidomimetics, small molecules (e.g. NCEs) and other drugs.

Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Examples of suitable methods based on the present description for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233. Libraries of compounds may be presented, for example, in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In a most preferred embodiment, the agent is an antibody which preferably specifically recognises IL-6 or IL-6R. Thus, the agent for use in the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement is suitably an antibody that interacts with (i.e. binds to or recognises) or modulates the activity of IL-6. Accordingly, there is provided the use of an antibody which is an inhibitor of IL-6 activity for the manufacture of a medicament for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement, and, in particular, associated with Goodpasture's syndrome. Also provided is a method for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement, and, in particular, associated with Goodpasture's syndrome in a subject comprising administering to said subject a therapeutically effective amount of an antibody which is an inhibitor of IL-6 activity.

In one example the antibodies selectively interact with IL-6. Most preferred are antibodies that specifically interact with IL-6, preferably human IL-6. Specifically interacting with (e.g. recognising or binding to) means that the antibodies have a greater affinity for IL-6 than for other polypeptides. Examples of suitable antibodies are those that inhibit the activity of IL-6 by binding to IL-6 in such a manner as to prevent it being biologically active, for example by preventing the binding of IL-6 to its receptor.

In another example the antibodies selectively interact with the IL-6 receptor, IL-6R. Selectively interacting with (e.g. recognising or binding to) means that the antibodies have a greater affinity for the IL-6R polypeptide than for other polypeptides. Examples of suitable antibodies are those that prevent IL-6 from binding to the IL-6 receptor. Accordingly, there is provided by the present invention the use of an anti-IL-6R antibody for the manufacture of a medicament for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement. Most preferably the disorder is Goodpasture's syndrome. Also provided is a method of treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement in a subject comprising administering to said subject a therapeutically effective amount of an anti-IL-6R antibody. In a preferred embodiment, the disorder is Goodpasture's syndrome.

In another embodiment, the agent is a nucleic acid which interacts with IL-6 or IL-6R. Accordingly, provided is the use of an IL-6 or IL-6R nucleic acid which interacts with or modulates the expression or activity of a mammalian IL-6 polypeptide for the manufacture of a medicament for the treatment and/or prophylaxis of glomerulonephritis associated with Goodpasture's syndrome, a vasculitic disorder, IgA nephropathy and an inflammatory disease with basement membrane involvement. Most preferably the disorder is Goodpasture's syndrome. In particular, IL-6 or IL-6R nucleic acid molecules may be used as anti-sense molecules, to alter the expression of their respective polypeptides by binding to complementary nucleic acids. IL-6 or IL-6R nucleic acids may be obtained using standard cloning techniques from for example genomic DNA or cDNA or can be synthesised using well known and commercially available techniques. The IL-6 or IL-6R nucleic acids may contain one or more nucleotide substitutions, additions or deletions into the nucleotide sequence of an IL-6 or IL-6R nucleic acid. Standard techniques known to those of skill in the art can be used to introduce mutations, including, for example, site-directed mutagenesis and PCR-mediated mutagenesis. An antisense nucleic acid according to the present invention includes a IL-6 or IL-6R nucleic acid capable of hybridising by virtue of some sequence complementarity to a portion of an RNA (preferably mRNA) encoding the respective polypeptide. The antisense nucleic acid can be complementary to a coding and/or non-coding region of an mRNA encoding such a polypeptide. Most preferably, the antisense nucleic acids result in inhibition of the expression of the IL-6 or IL-6R polypeptide. Thus, the present invention provides a method for the treatment and/or prophylaxis of MS comprising administering a therapeutically effective amount of an inhibitor of IL-6 activity wherein the inhibitor comprises at least eight nucleotides that are antisense to a gene or cDNA encoding a IL-6 or IL-6R polypeptide. The invention also provides the use of nucleic acids comprising at least eight nucleotides that are antisense to a gene or cDNA encoding a IL-6 or IL-6R polypeptide for the manufacture of a medicament for the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement, and in particular Goodpasture's syndrome.

IL-6 or IL-6R polypeptides or cells expressing said polypeptides can be used to produce antibodies, e.g. which specifically recognise said IL-6 or IL-6R polypeptides. The IL-6 and IL-6R polypeptides may be 'mature' polypeptides or biologically active fragments or derivatives thereof. IL-6 and IL-6R polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. IL-6 and IL-6R polypeptides may in some instances be part of a larger protein such as a fusion protein for example fused to an affinity tag. Antibodies generated against an IL-6 or IL-6R polypeptide may be obtained by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986. Many warm-blooded animals, such as rabbits, mice, rats, sheep, chickens, cows or pigs may be immunised. However, mice, rabbits, pigs and rats are generally preferred.

The term 'antibody' as used herein includes complete antibodies and functionally active fragments or derivatives thereof and may be, but are not limited to polyclonal, monoclonal, multi-valent, multi-specific, humanized or chimeric antibodies, single chain antibodies, Fab fragments, Fab' and F(ab')$_2$ fragments, fragments produced by a Fab expression library, anti-idiotypic (anti-Id) antibodies, and epitope-binding fragments of any of the above (see for example Holliger and Hudson, 2005, Nature Biotech. 23(9):1126-1136). Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD or IgA) or subclass of immunoglobulin molecule.

The antibodies for use in the invention may be produced by any suitable method known in the art. Such antibodies include, but are not limited to, polyclonal, monoclonal, humanized, phage display-derived antibodies or chimeric antibodies.

Monoclonal antibodies may be prepared by any method known in the art such as the hybridoma technique (Kohler & Milstein, Nature, 1975, 256:495-497), the trioma technique, the human B-cell hybridoma technique (Kozbor et al., Immunology Today, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA, 93(15), 7843-7848, WO 92/02551, WO2004/051268 and WO2004/106377.

Chimeric antibodies are those antibodies encoded by immunoglobulin genes that have been genetically engineered so that the light and heavy chain genes are composed of immunoglobulin gene segments belonging to different species.

Humanized antibodies are antibody molecules having one or more complementarity determining regions (CDRs) from a non-human species and a framework region from a human immunoglobulin molecule (see, for example, U.S. Pat. No. 5,585,089).

The methods for creating and manufacturing recombinant antibodies are well known in the art (see for example, Boss et al., U.S. Pat. No. 4,816,397; Cabilly et al., U.S. Pat. No. 6,331,415; Simmons et al., 2002, Journal of Immunological Methods, 263, 133-147; Shrader et al., WO 92/02551; Orlandi et al., 1989, Proc. Natl. Acad. Sci. USA, 86, 3833; Riechmann et al., 1988, Nature, 322, 323; Queen et al., U.S. Pat. No. 5,585,089; Adair, WO91/09967; Mountain and Adair, 1992, Biotechnol. Genet. Eng. Rev, 10, 1-142; Verma et al., 1998, J. Immunol. Methods, 216:165-181; Holliger and Hudson, 2005, Nature Biotech. 23(9):1126-1136).

The antibodies for use in the present invention can also be generated using various phage display methods known in the art and include those disclosed by Brinkman et al., 1995, J. Immunol. Methods, 182:41-50; Ames et al., 1995, J. Immunol. Methods, 184, 177-186; Kettleborough et al. 1994, Eur. J. Immunol., 24, 952-958; Persic et al., 1997, Gene, 187, 9-18; and Burton et al., 1994, Advances in Immunol., 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Also, transgenic mice, or other organisms, including other mammals, may be used to produce antibodies (see for example U.S. Pat. No. 6,300,129).

Antibody fragments and methods of producing them are well known in the art, see for example Verma et al., 1998, Journal of Immunological Methods, 216, 165-181.

Particular examples of antibody fragments for use in the present invention are Fab' fragments which possess a native or a modified hinge region. A number of modified hinge regions have already been described, for example, in U.S. Pat. No. 5,677,425, WO9915549, and WO9825971 and these are incorporated herein by reference Further examples of particular antibody fragments for use in the present invention include those described in International patent applications WO2005003169, WO2005003170 and WO2005003171. In particular, the modified antibody Fab fragments described in WO2005003169 are preferred.

The antibodies for use in the invention include analogues and derivatives that are modified, for example but without limitation, by the covalent attachment of any type of molecule. Preferably, said attachment does not impair immunospecific binding. Thus, an antibody for use in the present invention may be conjugated to one or more effector molecule(s). Preferably, an effector molecule may increase the half-life of the antibody in vivo, and/or reduce immunogenicity of the antibody and/or enhance the delivery of an antibody across an epithelial barrier to the immune system. Examples of suitable effector molecules of this type include polymers, dextran, hydroxypropylmethacrylamide (HPMA), albumin, albumin binding proteins or albumin binding compounds such as those described in WO2005117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide. See for example, Veronese and Pasut, 2005, Drug Discovery Today, 10(21):1451-1458; Pasut et al., 2004, Expert Opinion in Therapeutic Patents, 14(6):859-894.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for a review see Chapman, 2002, Advanced Drug Delivery Reviews, 54, 531-545). Thus, for example, where the product is intended to leave the circulation and penetrate tissue, for example for use in the treatment of glomerulonephritis, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971). In one example the antibody molecule of the present invention is a modified Fab fragment wherein the modification is the addition to the C-terminal end of its heavy chain of one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably, PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly (ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one example the effector molecule is PEG and is attached using the methods described in WO98/25971 and WO2004072116 whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

PEG is attached to these fragments by first reducing the interchain disulphide bond between the interchain cysteines of CL and CH1 and subsequently attaching the PEG to the free thiols. Once PEG is attached to the interchain cysteines there is no interchain disulphide linkage between the heavy and light chain. Suitable reducing agents for reducing the interchain disulphide bond are widely known in the art for example those described in Singh et al., 1995, Methods in Enzymology, 251, 167-73. Particular examples include thiol based reducing agents such as reduced glutathione (GSH), β-mercaptoethanol (β-ME), β-mercaptoethylamine (β-MA) and dithiothreitol (DTT). Other methods include using electrolytic methods, such as the method described in Leach et al., 1965, Div. Protein. Chem., 4, 23-27 and using photoreduction methods, such as the method described in Ellison et al., 2000, Biotechniques, 28 (2), 324-326. Preferably however, the reducing agent is a non-thiol based reducing agent, preferably one of the trialkylphosphine reducing agents (Ruegg U T and Rudinger, J., 1977, Methods in Enzymology, 47, 111-126; Burns J et al., 1991, J. Org. Chem., 56, 2648-2650; Getz et al., 1999, Analytical Biochemistry, 273, 73-80; Han and Han, 1994, Analytical Biochemistry, 220, 5-10; Seitz et al., 1999, Euro. J. Nuclear Medicine, 26, 1265-1273), particular examples of which include tris(2-carboxyethyl)phosphine (TCEP), tris butyl phosphine (TBP), tris-(2-cyanoethyl) phosphine, tris-(3-hydroxypropyl) phosphine (THP) and tris-(2-hydroxyethyl) phosphine. Most preferred are the reducing agents TCEP and THP. It will be clear to a person skilled in the art that the concentration of reducing agent can be determined empirically, for example, by varying the concentration of reducing agent and measuring the number of free thiols produced. Typically the reducing agent is used in excess over the antibody fragment for example between 2 and 1000 fold molar excess. Preferably the reducing agent is in 2, 3, 4, 5, 10, 100 or 1000 fold excess. In one embodiment the reductant is used at between 2 and 5 mM.

The reduction and PEGylation reactions may generally be performed in a solvent, for example an aqueous buffer solution such as acetate or phosphate, at around neutral pH, for example around pH 4.5 to around pH 8.5, typically pH 4.5 to 8, suitably pH6 to 7. The reactions may generally be performed at any suitable temperature, for example between about 5° C. and about 70° C., for example at room temperature. The solvent may optionally contain a chelating agent such as EDTA, EGTA, CDTA or DTPA. Preferably the solvent contains EDTA at between 1 and 5 mM, preferably 2 mM. Alternatively or in addition the solvent may be a chelating buffer such as citric acid, oxalic acid, folic acid, bicine, tricine, tris or ADA. The PEG will generally be employed in excess concentration relative to the concentration of the antibody fragment. Typically the PEG is in between 2 and 100 fold molar excess, preferably 5, 10 or 50 fold excess.

Where necessary, the desired product containing the desired number of PEG molecules may be separated from any starting materials or other product generated during the production process by conventional means, for example by chromatography techniques such as ion exchange, size exclusion, protein A, G or L affinity chromatography or hydrophobic interaction chromatography.

To identify inhibitors of IL-6 activity a number of different approaches may be taken by those skilled in the art. In one example inhibitors are identified by first identifying agents that interact with IL-6 or IL-6R and subsequently testing those agents to identify those that inhibit IL-6 activity. In one such example the agent is an antibody.

Agents that interact with IL-6 or IL-6R may be identified using any suitable method, for example by using a cell-free or cell-based assay system where the IL-6 or IL-6R polypeptide is contacted with a candidate agent and the ability of the candidate agent to interact with the polypeptide is determined. Preferably, the ability of a candidate agent to interact with a IL-6 or IL-6R polypeptide is compared to a reference range or control. If desired, this assay may be used to screen a plurality (e.g. a library) of candidate agents using a plurality of IL-6 or IL-6R polypeptide samples. In one example of a cell free assay, a first and second sample comprising native or recombinant IL-6 or IL-6R polypeptide are contacted with a candidate agent or a control agent and the ability of the candidate agent to interact with the polypeptide is determined by comparing the difference in interaction between the candidate agent and control agent. Preferably, the polypeptide is first immobilized, by, for example, contacting the polypeptide with an immobilized antibody which specifically recognizes and binds it, or by contacting a purified preparation of polypeptide with a surface designed to bind proteins. The polypeptide may be partially or completely purified (e.g. partially or completely free of other polypeptides) or part of a cell lysate. Further, the polypeptide may be a fusion protein comprising the IL-6 or IL-6R polypeptide or a biologically active portion thereof and a domain such as glutathionine-S-transferase or the Fc region of IgG1. Alternatively, the polypeptide can be biotinylated using techniques well known to those of skill in the art (e.g. biotinylation kit, Pierce Chemicals; Rockford, Ill.). The ability of the candidate agent to interact with the polypeptide can be determined by methods known to those of skill in the art, for example ELISA, BIAcore™, Flow cytometry or fluorescent microvolume assay technology (FMAT). In another example where a cell-based assay is used, a population of cells expressing IL-6 or IL-6R is contacted with a candidate agent and the ability of the candidate agent to interact with the polypeptide is determined. Preferably, the ability of a candidate agent to interact with IL-6 or IL-6R is compared to a reference range or control. The cell, for example, can be of eukaryotic origin (e.g. yeast or mammalian) and can express the IL-6 or IL-6R polypeptide endogenously or be genetically engineered to express the polypeptide. In some instances, the IL-6 or IL-6R polypeptide or the candidate agent is labelled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent. Alternative methods such as ELISA, flow cytometry and FMAT may also be used.

Agents which inhibit IL-6 activity may be identified by any suitable method, for example by:
 (i) comparing the activity of IL-6 in the presence of a candidate agent with the activity of said polypeptide in the absence of the candidate agent or in the presence of a control agent; and
 (ii) determining whether the candidate agent inhibits activity of IL-6.

Such assays can be used to screen candidate agents, in clinical monitoring or in drug development.

As described above, agents may be pre-screened where appropriate to identify agents (e.g. an antibody) that interact with IL-6 or IL-6R prior to screening those agents which bind for their ability to inhibit IL-6 activity.

In one example a cell-based assay system is used to identify agents capable of inhibiting the activity of IL-6. In one particular example, an assay used to identify inhibitors of IL-6 activity includes inhibition of the IL-6 dependent proliferation of the plasmacytoma cell line T1165 or the DS-1 cell line such as described in Sawamura et al. (1990, Growth Factors, 3, 181-190; Bock et al., 1993; Cytokine, 5, 480-489).

In another example inhibitors of IL-6 may down-regulate the expression of the IL-6 or IL-6R polypeptide, for example antisense inhibitors. Such inhibitors may be identified by any method known in the art. In one example such inhibitors are identified in a cell-based assay system. Accordingly, a population of cells expressing a IL-6 or IL-6R polypeptide or nucleic acid are contacted with a candidate agent and the ability of the candidate agent to alter expression of the IL-6 or IL-6R polypeptide or nucleic acid is determined by comparison to a reference range or control. In one example, populations of cells expressing a IL-6 or IL-6R polypeptide are contacted with a candidate agent or a control agent and the ability of the candidate agent to alter the expression of the IL-6 or IL-6R polypeptides or nucleic acids is determined by comparing the difference in the level of expression of the IL-6 or IL-6R polypeptides or nucleic acids between the treated and control populations of cells. If desired, this assay may be used to screen a plurality (e.g. a library) of candidate agents. The cell, for example, can be of eukaryotic origin (e.g. yeast or mammalian) and can express an IL-6 or IL-6R polypeptide endogenously or be genetically engineered to express a IL-6 or IL-6R polypeptide. The ability of the candidate agents to alter the expression of a said polypeptides or nucleic acids can be determined by methods known to those of skill in the art, for example and without limitation, by flow cytometry, radiolabelling, a scintillation assay, immunoprecipitation, Western blot analysis, Northern blot analysis or RT-PCR.

Agents that inhibit the activity of IL-6 may be identified or further tested, for example to determine therapeutically effective amounts in one or more animal models. Examples of suitable animals include, but are not limited to, mice, rats, rabbits, monkeys, guinea pigs, dogs and cats. Preferably, the animal used represents a model of glomerulonephritis associated with one or more disorders selected from the group consisting of Goodpasture's syndrome, a vasculitic disorder, Wegener's disease, IgA nephropathy and an inflammatory disease with basement membrane involvement, and, most preferably, Goodpasture's syndrome.

In one example where the agent inhibits the expression of IL-6 or IL-6R, a first and second group of mammals are administered with a candidate agent or a control agent and the ability of the candidate agent to inhibit the expression of IL-6 or IL-6R polypeptide or nucleic acid is determined by comparing the difference in the level of expression between the first and second group of mammals. Where desired, the expression levels of the IL-6 or IL-6R polypeptides or nucleic acid in the first and second groups of mammals can be compared to the level of IL-6 or IL-6R polypeptide or nucleic acid in a control group of mammals. The candidate agent or a control agent can be administered by means known in the art (e.g. orally, rectally or parenterally such as intraperitoneally or intravenously). Changes in the expression of a polypeptide or nucleic acid can be assessed by the methods outlined above. Models of glomerulonephritis associated with Goodpasture's disease are known in the art and are described in a review (Erwig et al., 2001, Curr. Opin. Nephrol. Hypertens. 10:341-347).

In another example, the inhibition of IL-6 activity can be determined by monitoring an amelioration or improvement in disease symptoms, a delayed onset or slow progression of the disease, for example but without limitation, a reduction in proteinuria. Techniques known to physicians familiar with glomerulonephritis associated with one or more disorders selected from the group consisting of Goodpasture's syndrome, a vasculitic disorder, Wegener's disease, IgA nephropathy and an inflammatory disease with basement membrane involvement can be used to determine whether a candidate agent has altered one or more symptoms associated with the disease.

As discussed herein, agents which interact with an IL-6 polypeptide find use in the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement. Most preferred is Goodpasture's syndrome. For such use the agents will generally be administered in the form of a pharmaceutical composition.

Thus, according to the invention there is provided a pharmaceutical composition comprising an agent which interacts with or modulates the expression or activity of with an IL-6 polypeptide and a pharmaceutically acceptable diluent, excipient and/or carrier. Pharmaceutical compositions may also find use as a vaccine and may comprise additional components acceptable for vaccine use and may additionally comprise one or more suitable adjuvants as known to the skilled person.

Hereinafter, the agents of use in the invention, and IL-6 polypeptides and IL-6 nucleic acids of use in treatment and/or prophylaxis are referred to as 'active agents'. When a reference is made herein to a method of treating or preventing a disease or condition using a particular active agent or combination of agents, it is to be understood that such a reference is intended to include the use of that active agent or combination of agents in the preparation of a medicament for the treatment and/or prophylaxis of the disease or condition. Thus, also provided is an anti-IL-6 antibody as an active agent for use in the therapy of glomerulonephritis associated with one or more disorders selected from the group consisting of Goodpasture's syndrome, a vasculitic disorder, Wegener's disease, IgA nephropathy and an inflammatory disease with basement membrane involvement. Most preferred is Goodpasture's syndrome. Such an antibody may be presented attached to or associated with an effector molecule as previously described.

The composition will usually be supplied as part of a sterile, pharmaceutical composition that will normally include a pharmaceutically acceptable carrier. This composition may be in any suitable form (depending upon the desired method of administering it to a patient).

Active agents of the invention may be administered to a subject by any of the routes conventionally used for drug administration, for example they may be administered parenterally, orally, topically (including buccal, sublingual or transdermal, or using particle-mediated intracellular delivery directly into cells of the skin) or by inhalation. Particle-mediated delivery is described by Haynes, J R, 2004, Expert Opinion on Biological Therapy, 4:889-900. The most suitable route for administration in any given case will depend on the particular active agent, the disorder involved, the subject, and the nature and severity of the disease and the physical condition of the subject.

The active agents may be administered in combination, e.g. simultaneously, sequentially or separately, with one or more other therapeutically active, e.g. anti-inflammatory, compounds.

Pharmaceutical compositions may be conveniently presented in unit dose forms containing a predetermined amount of an active agent of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399, 163; 5,383,851; 5,312,335; 5,064,413; 4,941,880; 4,790,824;

or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions of the invention can be formulated to ensure proper distribution in vivo. For example, the blood-brain barrier excludes many highly hydrophilic compounds and it may be preferable to deliver pharmaceutical compositions in liposomes. Thus, in one embodiment of the invention, the active agents of the invention are formulated in liposomes; in a more preferred embodiment, the liposomes include a targeting moiety.

Formulations of active agents may be delivered in fluorocarbons as pulmonary, topical or opthalmological and include active agent-in-fluorocarbon suspensions, reverse water-in-fluorocarbon emulsions, oil-in-fluorocarbon emulsions, multiple emulsions, microemulsions, fluorocarbon gels, fluorinated liposomes and fluorinated tubules.

The compositions may be presented in unit-dose or multi-dose containers, for example in sealed ampoules and vials and to enhance stability, may be stored in a freeze-dried (lyophilized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included the sterile liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

Pharmaceutical compositions adapted for vaginal administration may be presented as pessaries, tampons, creams, gels, pastes, foams or spray compositions. These may comprise emollients or bases as commonly used in the art.

The dosage to be administered of an active agent will vary according to the particular active agent, the disorder involved, the subject, and the nature and severity of the disease and the physical condition of the subject, the age, weight and gender of the subject, diet, time and frequency of administration, drug combination(s), reaction sensitivities, tolerance/response to therapy, and the selected route of administration; and that a physician will ultimately determine appropriate dosages to be used. This dosage may be repeated as often as appropriate. Generally, a therapeutically effective amount will be from 0.01 mg/kg to 100 mg/kg, preferably 0.1 mg/kg to 20 mg/kg. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months. If side effects develop the amount and/or frequency of the dosage can be altered or reduced, in to accordance with normal clinical practice.

Pharmaceutical compositions may be conveniently presented in unit dose forms containing a predetermined amount of an active agent of the invention per dose. In particular, the dose at which the antibody molecule of the present invention is administered depends on the nature of the condition to be treated, the extent of the inflammation present and on whether the antibody molecule is being used prophylactically or to treat an existing condition.

For the treatment and/or prophylaxis of glomerulonephritis associated with one or more disorders selected from the group consisting of Goodpasture's syndrome, a vasculitic disorder, Wegener's disease, IgA nephropathy and an inflammatory disease with basement membrane involvement, and, in particular, in humans and animals pharmaceutical compositions comprising antibodies can be administered to patients (e.g., human subjects) at therapeutically or prophylactically effective dosages (e.g. dosages which result in a reduction in glomerulonephritis) using any suitable route of administration, such as injection and other routes of administration known in the art for antibody-based clinical products. The compositions may contain from 0.1% by weight, preferably from 10-60%, or more, by weight, of the active agent of the invention, depending on the method of administration.

Compositions may be administered individually to a patient or may be administered in combination (e.g. simultaneously, sequentially or separately) with other agents, drugs or hormones.

In another example, where the inhibitor is a nucleic acid this may be administered via gene therapy (see for example Hoshida, T. et al., 2002, Pancreas, 25:111-121; Ikuno, Y. 2002, Invest. Opthalmol. Vis. Sci. 2002 43:2406-2411; Bollard, C., 2002, Blood 99:3179-3187; Lee E., 2001, Mol. Med. 7:773-782). Gene therapy refers to administration to a subject of an expressed or expressible nucleic acid. In one example this is either the IL-6 or IL-6R nucleic acid or portions thereof. Any of the methods for gene therapy available in the art can be used according to the present invention.

Delivery of the therapeutic nucleic acid into a patient can be direct in vivo gene therapy (i.e. the patient is directly exposed to the nucleic acid or nucleic acid-containing vector) or indirect ex vivo gene therapy (i.e. cells are first transformed with the nucleic acid in vitro and then transplanted into the patient).

For example for in vivo gene therapy, an expression vector containing the IL-6 or IL-6R nucleic acid may be administered in such a manner that it becomes intracellular, i.e. by infection using a defective or attenuated retroviral or other viral vectors as described, for example, in U.S. Pat. No. 4,980,286 or by Robbins et al., 1998, Pharmacol. Ther. 80:35-47.

The various retroviral vectors that are known in the art are such as those described in Miller et al. (1993, Meth. Enzymol. 217:581-599) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (1999, Human Gene Therapy, 10:2451-2459). Chimeric viral vectors that can be used are those described by Reynolds et al. (1999, Molecular Medicine Today, 1:25-31). Hybrid vectors can also be used and are described by Jacoby et al. (1997, Gene Therapy, 4:1282-1283).

Direct injection of naked DNA or through the use of microparticle bombardment (e.g. Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu & Wu, 1987, J. Biol. Chem., 262:4429-4432) can be used to target cell types which specifically express the receptors of interest.

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as haematopoietic stem or progenitor cells.

Cells into which a IL-6 or IL-6R nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryotcytes, granulocytes, haematopoietic cells or progenitor cells, and the like.

In a one aspect, the pharmaceutical composition of the present invention comprises an IL-6 or IL-6R nucleic acid, said nucleic acid being part of an expression vector that expresses an IL-6 or IL-6R polypeptide or chimeric protein thereof in a suitable host. In particular, such a nucleic acid has a promoter operably linked to the polypeptide coding region, said promoter being inducible or constitutive (and, optionally, tissue-specific).

Recombinant IL-6 polypeptides may be prepared by processes well known in the art from genetically engineered host cells comprising expression systems. Accordingly, the present invention also relates to expression systems which comprise an IL-6 polypeptide or IL-6 nucleic acid, to host cells which are genetically engineered with such expression systems and to the production of IL-6 polypeptides by recombinant techniques. Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK.

For recombinant IL-6 polypeptide production, host cells can be genetically engineered to incorporate expression systems or portions thereof for IL-6 nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

Representative examples of host cells include bacterial cells e.g. *E. Coli, Streptococci, Staphylococci, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, HEK 293, BHK and Bowes melanoma cells; and plant cells.

A wide variety of expression systems can be used, such as and without limitation, chromosomal, episomal and virus-derived systems, e.g. vectors derived from bacterial plasmids, from bacteriophage, from transposons, from yeast episomes, from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a nucleic acid to produce a polypeptide in a host may be used. The appropriate nucleic acid sequence may be inserted into an expression system by any variety of well-known and routine techniques, such as those set forth in Sambrook et al., supra. Appropriate secretion signals may be incorporated into the IL-6 polypeptide to allow secretion of the translated protein into the lumen of the endoplasmic reticulum, the periplasmic space or the extracellular environment. These signals may be endogenous to the IL-6 polypeptide or they may be heterologous signals.

IL-6 polypeptides can be recovered and purified from recombinant cell cultures or from other biological sources by well-known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an IL-6 polypeptide can be used to deplete a sample comprising an IL-6 polypeptide of said polypeptide or to purify said polypeptide. Techniques well-known in the art, may be used for refolding to regenerate native or active conformations of the IL-6 polypeptides when the polypeptides have been denatured during isolation and or purification. In the context of the present invention, IL-6 polypeptides can be obtained from a biological sample from any source, such as and without limitation, a blood sample.

IL-6 or IL6R nucleic acids may be obtained using standard cloning and screening techniques, from a cDNA library derived from mRNA in human cells, using expressed sequence tag (EST) analysis (Adams, M. et al., 1991, Science, 252:1651-1656; Adams, M. et al., 1992, Nature 355: 632-634; Adams, M. et al., 1995, Nature, 377:Suppl: 3-174). IL-6 nucleic acids can also be obtained from natural sources such as genomic DNA libraries or can be synthesized using well known and commercially available techniques. The IL-6 or Il-6R nucleic acids comprising coding sequence for IL-6 or IL-6R polypeptides can be used for the recombinant production of said polypeptides. The IL-6 or IL-6R nucleic acids may include the coding sequence for the mature polypeptide, by itself; or the coding sequence for the mature polypeptide in reading frame with other coding sequences, such as those encoding a leader or secretory sequence, a pre-, pro- or pre-pro-protein sequence, a cleavable sequence or other fusion peptide portions, such as an affinity tag or an additional sequence conferring stability during production of the polypeptide. Preferred affinity tags include multiple histidine residues (for example see Gentz et al., 1989, Proc. Natl. Acad. Sci. USA 86:821-824), a FLAG tag, HA tag or myc tag. The IL-6 nucleic acids may also contain non-coding 5' and 3' sequences, such as transcribed, non-translated sequences, splicing and polyadenylation signals, ribosome binding sites and sequences that stabilize mRNA.

IL-6 or IL-6R polypeptide derivatives above can be created by introducing one or more nucleotide substitutions, additions or deletions into the nucleotide sequence of an IL-6 or IL-6R nucleic acid such that one or more amino acid substitutions, additions or deletions are introduced into the encoded protein. Standard techniques known to those of skill in the art can be used to introduce mutations, including, for example, site-directed mutagenesis and PCR-mediated mutagenesis. Preferably, conservative amino acid substitutions are made at one or more predicted non-essential amino acid residues.

An IL-6 or IL-6R nucleic acid encoding an IL-6 or IL-6R polypeptide, including homologues and orthologues from species other than human, may be obtained by a process which comprises the steps of screening an appropriate library under stringent hybridisation conditions with a labelled probe and isolating full-length cDNA and genomic clones containing said nucleic acid sequence. Such hybridisation techniques are well-known in the art. One example of stringent hybridisation conditions is where attempted hybridisation is carried out at a temperature of from about 35° C. to about 65° C. using a salt solution of about 0.9M. However, the skilled person will be able to vary such conditions as appropriate in order to take into account variables such as probe length, base composition, type of ions present, etc. For a high degree of selectivity, relatively stringent conditions such as low salt or high temperature conditions, are used to form the duplexes. Highly stringent conditions include hybridisation to filter-bound DNA in 0.5M NaHPO$_4$, 7% sodium dodecyl sulphate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., New York, at p. 2.10.3). For some applications, less stringent conditions for duplex formation are required. Moderately stringent conditions include washing in 0.2×SSC/0.1% SDS at 42° C. (Ausubel et al., 1989, supra). Hybridisation conditions can also be rendered more stringent by the addition of increasing amounts of formamide, to destabilise the hybrid duplex. Thus, particular hybridisation conditions can be readily manipulated, and will generally be chosen as appropriate. In general, convenient hybridisation temperatures in the presence of 50% formamide are: 42° C. for a probe which is 95-100% identical to the fragment of a gene encoding a polypeptide as defined herein, 37° C. for 90-95% identity and 32° C. for 70-90% identity.

One skilled in the art will understand that, in many cases, an isolated cDNA sequence will be incomplete, in that the region coding for the polypeptide is cut short at the 5' end of the cDNA. This is a consequence of reverse transcriptase, an enzyme with inherently low processivity (a measure of the ability of the enzyme to remain attached to the template during the polymerization reaction), failing to complete a DNA copy of the mRNA template during $1^{st}$ strand cDNA synthesis.

Methods to obtain full length cDNAs or to extend short cDNAs are well known in the art, for example RACE (Rapid amplification of cDNA ends; e.g. Frohman et al., 1988, Proc. Natl. Acad. Sci. USA 85:8998-9002). Recent modifications of the technique, exemplified by the Marathon™ technology (Clontech Laboratories Inc.) have significantly simplified the search for longer cDNAs. This technology uses cDNAs prepared from mRNA extracted from a chosen tissue followed by the ligation of an adaptor sequence onto each end. PCR is then carried out to amplify the missing 5'-end of the cDNA using a combination of gene specific and adaptor specific oligonucleotide primers. The PCR reaction is then repeated using nested primers which have been designed to anneal with the amplified product, typically an adaptor specific primer that anneals further 3' in the adaptor sequence and a gene specific primer that anneals further 5' in the known gene sequence. The products of this reaction can then be analysed by DNA sequencing and a full length cDNA constructed either by joining the product directly to the existing cDNA to give a complete sequence, or carrying out a separate full length PCR using the new sequence information for the design of the 5' primer.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

FIGURE LEGENDS

FIG. 1

Histochemistry showing typical crescentic glomerulonephritis in the kidney of CD1 mice 12 weeks after immunisation with recombinant α3(IV)NC1. The arrows indicate a fibrous crescent.

EXAMPLE 1

Preparation of Recombinant Alpha 3 Chain of Type IV Collagen [α3(Iv)NC1]

Recombinant α3(IV)NC1 was prepared as described by Reynolds et al. (Reynolds et al., 2005, J Am Soc Nephrol., 16:1350-1359).

EXAMPLE 2

Murine Model of Goodpasture's Syndrome

Figure 1:
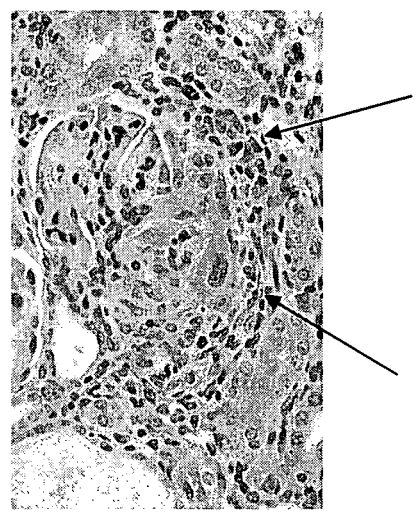
Figure 2:
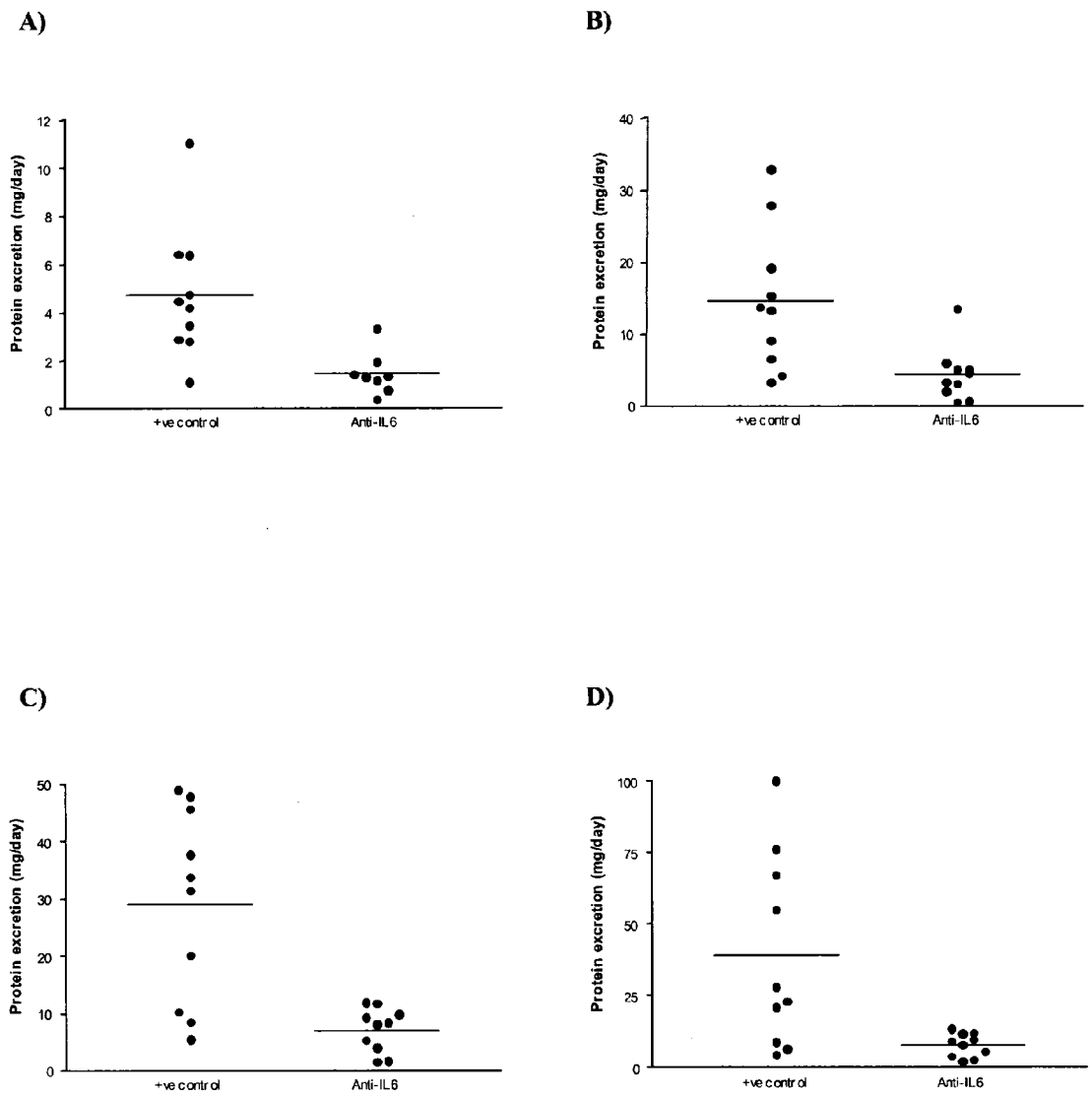
FIG. 2 shows the effect of treatment with an anti-IL-6 antibody on proteinuria of CD1 mice 3 weeks [panel (A)], 6 weeks [panel (B)], 9 weeks [panel (C)] or 12 weeks [panel (D)] after immunisation with recombinant α3(IV)NC1.

CD1 mice were immunised with recombinant α3(IV)NC1 in CFA s.c. at the base of the tail followed by 2 boosts in IFA s.c. 1 and 2 weeks later. Mice developed circulating and deposited anti-glomerular basement membrane antibodies, proteinuria and focal proliferative glomerulonephritis by week 6 after injection which progressed to severe crescentic glomerulonephritis by week 12. Histology from an immunised animal showing marked glomerular scarring with fibrous crescents, tubulointerstitial scarring with tubular atrophy, and tubulointerstitial inflammation in the kidney is shown in FIG. 1.

EXAMPLE 3

IL-6 Antibody Treatment

Groups of CD1 mice (n=10) were given irrelevant antibody (positive control) or anti-IL-6 monoclonal antibody at a dose of 30 mg/kg (subcutaneously) weekly for 12 weeks from the day prior to immunisation with recombinant α3(IV)NC1.

Figure 3:
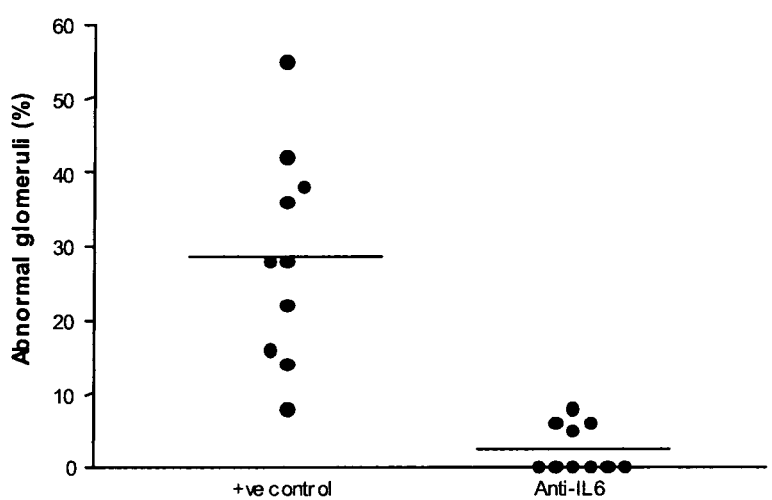
FIG. 3 shows the effect of treatment with an anti-IL-6 antibody on renal abnormalities of CD1 mice 12 weeks after immunisation with recombinant α3(IV)NC1.

Animals were placed in metabolic cages for 24 hours every 3 weeks, with free access to food and water, to allow collection of urine. Proteinuria in the urine was detected by the sulphosalicylic acid method (Khan et al., 2005, Kidney Int., 67: 1812-1820). Animals given the anti-IL-6 mAb showed a marked reduction in proteinuria when compared to positive controls as shown in FIG. 2A-D. At 12 weeks after immunisation proteinuria levels in anti-IL-6 treated mice was only 8 mg/day compared with 39 mg/day in mice treated with the irrelevant control antibody. The number of glomerular abnormalities was also reduced in mice treated with the anti-IL-6 antibody as shown in FIG. 3 (control, 29% versus anti-IL-6 mAb, 2%).

The results suggest that experimental autoimmune glomerulonephritis can be reliably induced in the CD1 mouse, and that anti-IL-6 mAb is effective in the prevention of glomerular injury in this model. Thus, the results show the importance of the role of IL-6 in the development of experimental autoimmune glomerulonephritis and indicate that strategies targeting IL-6 may provide a novel approach in the treatment of human glomerulonephritis.

The invention claimed is:

1. A method for treating Goodpasture's syndrome or Wegener's disease in a human, the method comprising administering to the human a therapeutically effective amount of an antibody or functionally-active fragment thereof which inhibits activity of a human IL-6 polypeptide.

2. The method according to claim 1, wherein the antibody is monoclonal, polyclonal, chimeric, humanised or bispecific.

3. The method according to claim 1, wherein the disorder is Goodpasture's syndrome.

4. The method according to claim 1, wherein the disorder is Wegener's disease.

5. The method according to claim 1, wherein said antibody or functionally-active fragment has an effector molecule attached thereto, wherein the effector molecule is a synthetic or a naturally occurring polymer, branched or unbranched polysaccharide, hydroxypropylmethacrylamide (HPMA), albumin, albumin binding protein or albumin binding compound.

6. The method according to claim 5, wherein the naturally occurring polymer is an optionally substituted straight or branched chain polyalkylene, polyalkenylene or polyoxyalkylene polymer or a branched or unbranched polysaccharide.

7. The method according to claim 5, wherein the naturally occurring polymer, is lactose, amylose, dextran, glycogen or any derivative thereof.

8. The method of claim 5, wherein the synthetic polymer is optionally substituted straight or branched chain poly(ethyleneglycol), poly(propyleneglycol) poly(vinylalcohol) or any derivative thereof.

9. The method of claim 8, wherein the optionally substituted straight or branched chain poly(ethyleneglycol) is methoxypoly(ethyleneglycol) or a derivative thereof.

* * * * *